United States Patent [19]

Iwata et al.

[11] Patent Number: 5,912,139
[45] Date of Patent: Jun. 15, 1999

[54] TEST STRIP

[75] Inventors: Ken Iwata; Kazue Kawahara; Hiroshi Nakajima, all of Kyoto, Japan

[73] Assignee: Unitika, Ltd., Hyogo, Japan

[21] Appl. No.: 08/897,626

[22] Filed: Jul. 21, 1997

[30] Foreign Application Priority Data

Jul. 23, 1996 [JP] Japan .................................. 8-193071

[51] Int. Cl.$^6$ ............................... C12Q 1/32; C12Q 1/54; C12Q 1/60; C12Q 1/42
[52] U.S. Cl. ............................... 435/26; 435/14; 435/11; 435/21; 435/970; 435/975
[58] Field of Search .................................. 435/26, 14, 11, 435/21, 970, 975

[56] References Cited

U.S. PATENT DOCUMENTS

| | | | |
|---|---|---|---|
| 3,992,158 | 11/1976 | Przybylowicz et al. | 435/26 |
| 4,774,192 | 9/1988 | Terminiello et al. | 435/26 |
| 4,786,589 | 11/1988 | Rounds | 435/26 |
| 4,791,057 | 12/1988 | Misaki et al. | 435/26 |
| 5,170,799 | 12/1992 | Nagase et al. | 435/26 |
| 5,290,683 | 3/1994 | Israel et al. | 435/26 |

FOREIGN PATENT DOCUMENTS

| | | |
|---|---|---|
| 0154409 | 11/1985 | European Pat. Off. . |
| 0456098 | 11/1991 | European Pat. Off. . |
| 0522875 | 1/1993 | European Pat. Off. . |
| 0556725 | 8/1993 | European Pat. Off. . |
| 53-101490 | 2/1977 | Japan . |
| 59-061777 | 4/1984 | Japan . |
| 61-260896 | 11/1986 | Japan . |
| 1-171498 | 7/1989 | Japan . |
| WO 9508639 | 3/1995 | WIPO . |

OTHER PUBLICATIONS

Yuan et al; Analytica Chimica Acta, V. 134, pp. 47–53, (1982). Month not available.
Journal of Biochemistry, vol. 96, pp. 1–8 (1984).
Rinsyo Kagaku (Japanese Journal of Chinical Chemistry), vol. 19, pp. 290–299 (1990) Month not available.

*Primary Examiner*—Louise N. Leary
*Attorney, Agent, or Firm*—Sughrue, Mion, Zinn, Macpeak & Seas, PLLC

[57] ABSTRACT

A test strip which comprises a carrier, a dehydrogenase, diaphorase, a fluorescent chromogen, and NAD or NADP. The test strip provides high sensitivity and high accuracy measurement, and have excellent storage stability.

20 Claims, No Drawings

TEST STRIP

FIELD OF THE INVENTION

This invention relates to a test strip for the measurement of trace components in samples, and more particularly, to a test strip which can determine trace components in samples gathered from the living body simply and easily and with high sensitivity based on a fluorescence measurement.

BACKGROUND OF THE INVENTION

In recent years, reagents utilizing enzyme reactions have broadly been used for inspecting and diagnosing morbid states, instead of conventional chemical reagents.

Each of these enzyme reaction-aided reagents utilizes the properties of enzymes to convert a specific component in the living body into a detectable substance. In general, in such an assay system, a substance (A) to be measured is converted into an intermediate product (I-1) using an enzyme (a) specific for the substance, further converted into another intermediate product (I-2) by allowing another enzyme (i-1) specific for the intermediate product (I-1) to exert its action and, by repeating such reactions, the substance (A) to be measured is ultimately converted into a detectable substance (F). Then, the detectable substance (F) is determined based on changes in color tone measured with a spectrophotometer or a fluorophotometer, or with the naked eye.

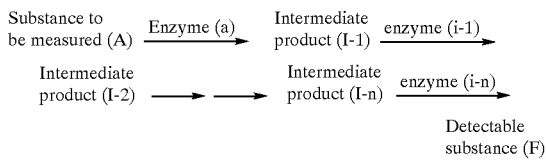

In such reagents, NAD and its reduced form (NADH), its analogous compound NADP and its reduced form (NADPH), are broadly used as the detectable substance (F) (these compounds hereinafter are generally referred to as "nicotine nucleotides"). Since changes in absorbance at an ultraviolet region (around 340 nm) are observed in these nicotine nucleotides, reagents have been proposed in which the formation or decrease of nicotine nucleotides is measured using a spectroscope. Also, a large number of reports have been published on the use of reagents characterized in that, by reacting diaphorase with the NADH or NADPH thus formed, tetrazolium is converted into formazan and measured at a visible range (for example, bile acid (JP-A-60-214900, and Rinsyo Kagaku (Japanese Journal of Clinical Chemistry), vol. 19, pp. 290–299 (1990); the term "JP-A" as used herein means an "unexamined published Japanese patent application"), triglyceride (JP-A-55-14899), alcohol (JP-B-4-3947; the term "JP-B" as used herein means an "examined Japanese patent publication), amylase (JP-B-63-37640), creatine kinase (JP-A- 58-16699 and JP-B-4-70000), polyamine (JP-B-6-68490), glucose (JP-B-7-34757) and benzylamine (JP-A-7-184693)).

In addition, in order to improve the measuring accuracy of nicotine nucleotides, several reagents have been proposed in which resazulin is converted into fluorescence-developing resorufine by the action of diaphorase, which is measured based on its fluorescence strength. For example, a reagent for measuring alanine prepared by dissolving NAD, resazulin sodium salt, diaphorase and alanine dehydrogenase in a carbonate buffer of pH 9.0 [Journal of Biochemistry, vol. 96, pp. 1–8 (1984)] and a reagent for measuring bile acid prepared by dissolving 3α—OH steroid dehydrogenase, NAD, resazulin sodium salt and diaphorase in a buffer of pH 3 to 13 (JP-B-56-39199) have been proposed.

However, because an adequate quantitative evaluation cannot be obtained by such reagents which employ a fluorescence-developing substance, a method has been proposed in which a sample containing bile acid as a substance to be measured is treated at high temperature (for example at 67° C. for 20 minutes) and then measured using the aforementioned reagent, in order to improve its quantitative analytic performance [JP-B-56-39119 and Rinsyo Kagakushi (Japanese Journal of Clinical Chemistry), vol. 4, pp. 312–318 (1976)]. It has been pointed out, however, that even such a method has a bile acid recovery ratio of only about 90%. In addition, due to the use of a fluorescent substance in the measurement, impurities in the samples and reagents thus used tend to interfere in the measurement. Therefore, there is a large deviation in the measured value (JP-B-59-13197).

SUMMARY OF THE INVENTION

It is therefore an object of the present invention is to provide a test strip which can measure substances with higher sensitivity and accuracy by increasing the recovery ratio of the substances being measured.

With the aim of solving the aforementioned problems, the present inventors have conducted extensive studies and, as the result, have found that substances can be measured with markedly high sensitivity and accuracy when fluorescence reagents conventionally used in liquid form are processed into test strips. The present invention has been accomplished on the basis of this finding.

Accordingly, the present invention has been achieved by providing a test strip which comprises a carrier, a dehydrogenase, diaphorase, a fluorescent chromogen and NAD or NADP.

The test strip of the present invention can measure samples with high sensitivity and high accuracy. Also, the test strip of the present invention has excellent storage stability.

Other objects and advantages of the present invention will become apparent in the following description and Examples.

DETAILED DESCRIPTION OF THE INVENTION

The dehydrogenase for use in the present invention acts in a specific fashion on a substance to be measured (A) or on an intermediate product derived from the substance to be measured (A) by one or several enzyme reaction steps. Examples of such combinations include glucose 6-phosphate dehydrogenase for glucose 6-phosphate, glycerol 3-phosphate dehydrogenase for glycerophosphoric acid, glycerol dehydrogenase for glycerol, phenylalanine dehydrogenase for phenylalanine, leucine dehydrogenase for leucine, alanine dehydrogenase for alanine, hydroxysteroid dehydrogenase for androsterone, cholesterol dehydrogenase for cholesterol and fucose dehydrogenase for fucose.

The fluorescent chromogen for use in the present invention is not particularly limited as long as it fluoresces when reduced by the action of diaphorase in the presence of NADH or NADPH. It is particularly desirable to use resazulin or alamar blue, because these substances have high fluorescence strength and are stable in air in both oxidized and reduced forms.

The diaphorase for use in the present invention is not particularly limited with regard to its biological origin as a supply source, and examples thereof include microorganism sources such as *Bacillus stearothermophilus, Clostridium kluyveri* and others apparent to one of ordinary skill in the art, as well as animal sources such as porcine heart and others apparent to one of ordinary skill in the art. Of these diaphorases, diaphorase produced by a thermophilic microorganism, e.g., diaphorase produced by *Bacillus stearothermophilus,* is desirable because of its excellent storage stability.

In addition, in order to improve the quantitative determination efficiency and recovery ratio of the substance to be measured (A), the diaphorase for use in the present invention may have a reaction equilibrium constant (K value) of 1 or more, preferably 10 or more, more preferably 100 or more, in the direction from the oxidized form of the fluorescent chromogen and the reduced form nicotine nucleotide (NADH or NADPH) toward the reduced form of the fluorescent chromogen and the oxidized form of the nicotine nucleotide (NAD or NADP), which is calculated using the following equation. For this purpose, it is desirable to use, for example, diaphorase I or diaphorase II produced by *Bacillus stearothermophilus.*

$$K = \frac{(\text{oxidized form nicotine nucleotide})(\text{reduced form fluorescent chromogen})}{(\text{reduced form nicotine nucleotide})(\text{oxidized form fluorescent chromogen})}$$

It is desirable to blend these components in such amounts that the enzyme reaction from the substance to be measured (A) to the reduced form fluorescent chromogen progresses at a ratio of 90% or more, preferably 97% or more, more preferably 99% or more. For this purpose, diaphorase is used in an amount such that a diaphorase solution having a concentration of from 0.1 to 1,000,000 units per liter, preferably from 0.1 to 10,000 units per liter, more preferably from 1 to 1,000 units per liter, may be used in an amount of from 0.1 to 10,000 μl, preferably from 1 to 1,000 μl, more preferably from 1 to 100 μl, per 100 cm² of the test strip. The dehydrogenase may be used in a concentration similar to that of the diaphorase. The NAD or NADP is used in an amount such that a solution having a concentration of from 0.001 nM to 200 mM, preferably from 0.1 nM to 50 mM, may be used in an amount of from 0.1 to 10,000 μl, preferably from 1 to 1,000 μl, more preferably from 1 to 100 μl, per 100 cm² of the test strip.

The fluorescent chromogen may be used in an amount of from 0.01 to 500 mg, preferably from 0.1 to 100 mg, more preferably from 0.1 to 50 mg, per 100 cm² of the test strip. In this case, the amount of the fluorescent chromogen, if too small, would reduce fluorescence, and if too large, would result in an insoluble form and thus cause reduced accuracy.

According to the present invention, when the substance to be measured (A) is not a substrate of the dehydrogenase, the test strip may be impregnated with various enzymes (a, i-1, i-2, i-n-2) which are necessary to convert the substance to be measured (A) into a substance which is a substrate of the dehydrogenase. Illustrative examples of a combination of the substance to be measured (A) with such enzymes include glucose to be measured and enzymes in accordance with the following reaction scheme (1) to enable the determination of glucose.

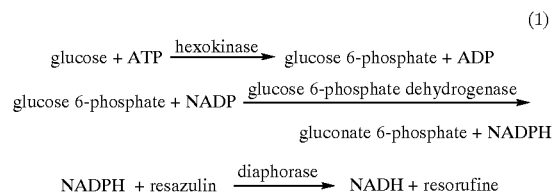

When glycerol is being measured, enzymes may be used in accordance with the following reaction scheme (2) or (3) so that glycerol can be determined.

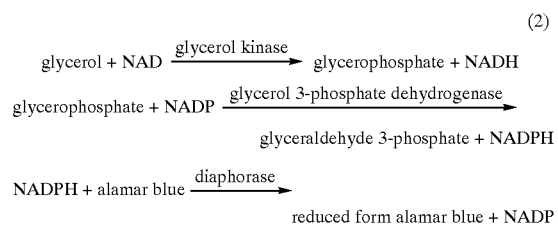

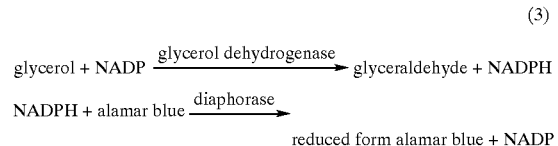

When triglyceride is being measured, enzymes may be used in a system where glycerol is formed in accordance with the following reaction scheme (4), and then the glycerol thus formed is determined in accordance with the aforementioned reaction scheme (2) or (3).

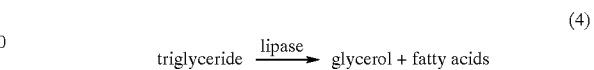

When phenylalanine is being measured, enzymes may be used in accordance with the following reaction scheme (5) to enable the determination of phenylalanine.

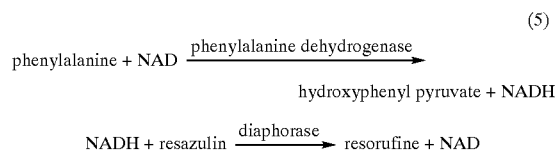

When leucine is being measured, enzymes may be used in accordance with the following reaction scheme (6) to enable the determination of leucine.

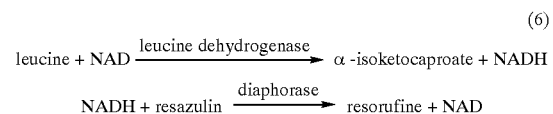

When alanine is being measured, enzymes may be used in accordance with the following reaction scheme (7) to enable the determination of alanine.

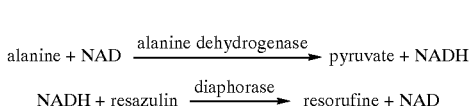

(7)

When cholesterol is being measured, enzymes may be used in accordance with the following reaction scheme (8) to enable the determination of cholesterol.

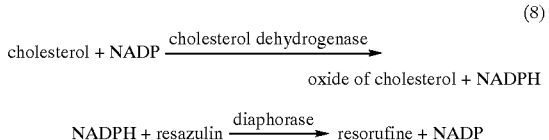

(8)

When fucose is being measured, enzymes may be used in accordance with the following reaction scheme (9) to enable the determination of fucose.

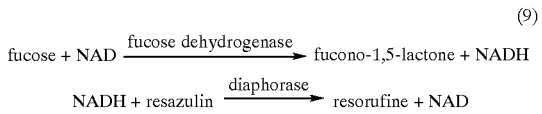

(9)

When creatine phosphate or creatine kinase is being measured, enzymes may be used in accordance with the following reaction scheme (10) to enable the determination of creatine phosphate or creatine kinase.

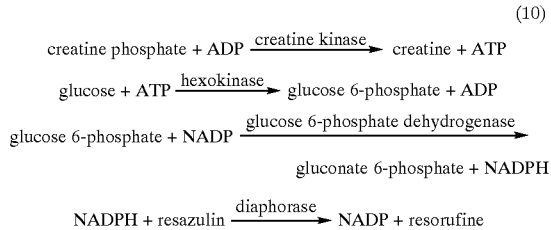

(10)

In this case, the concentration of each enzyme present in the test strip may be within the same range as the diaphorase. Also, ATP, NADP, NAD, or ADP may be used in an amount such that a solution having a concentration of from 0.1 to 100 mM, preferably from 0.1 to 20 mM, is used in an amount of from 0.1 to 10,000 μl, preferably from 1 to 1,000 μl, more preferably from 1 to 100 μl, per 100 cm² of the test strip.

According to the present invention, the test strip may contain a buffer for use in pH adjustment, an activating agent, a stabilizing agent, a viscosity-improving agent and other additives as needed.

Illustrative examples of the buffer include Tris, potassium phosphate, imidazole, triethanolamine, glycine and the like and, depending on the items to be tested, Good's buffers such as 2-morpholinoethanesulfonic acid (MES), N,N-bis (2-hydroxyethyl)-2-aminoethanesulfonic acid (BES), N-cyclohexyl-2-aminoethanesulfonic acid (CHES) and others apparent to one of ordinary skill in the art can be used.

Illustrative examples of the activating agent include nonionic, anionic or cationic surfactant, such as Triton X 100®, Tween 20® and others apparent to one of ordinary skill in the art. Since these surfactants improve the compatibility of the fluorescent chromogen with other water-soluble components, they contribute to the storage stability of the test strips and the reduction of blank values. These activating agents may be used in a concentration such that a solution having a activating agent concentration of from 0.001 to 20%, preferably from 0.01 to 5%, is used in an amount of from 0.1 to 10,000 μl, preferably from 1 to 1,000 μl, more preferably from 1 to 100 μl, per 100 cm² of the test strip.

Illustrative examples of the stabilizing agent include proteins such as bovine serum albumin and others apparent to one of ordinary skill in the art, saccharides such as maltose, glucose, sucrose and the like, high molecular weight compounds such as polyethylene glycol and others apparent to one of ordinary skill in the art and metal ions such as of magnesium, potassium, calcium and others apparent to one of ordinary skill in the art. These metal ions may also act as enzyme activators. Ethylenediaminetetraacetic acid (EDTA), ethyleneglycol bis-(β-aminoethyl ether) tetraacetic acid (EGTA) and others apparent to one of ordinary skill in the art may also be used. These stabilizing agents may be used in a concentration such that a saccharide solution having a saccharide concentration of from 0.1 to 50% (preferably from 1 to 25%), a protein solution having a protein concentration of from 0.001 to 50% (preferably from 0.1 to 25%), a metal ion solution having a metal ion concentration of from 0.001 to 10 mM (preferably from 0.1 to 10 mM), or an EDTA or EGTA solution having an EDTA or EGTA concentration of from 0.001 to 10 mM (preferably from 0.1 to 2 mM), is used in an amount of from 0.1 to 10,000 μl, preferably from 1 to 1,000 μl, more preferably from 1 to 100 μl, per 100 cm² of the test strip.

The carrier for use in the test strip of the present invention includes known carriers made of high molecular weight materials, and illustrative examples thereof include paper and non-woven fabric made of natural and synthetic fibers, as well as membrane filters and others apparent to one of ordinary skill in the art. The membrane filters include nitrocellulose membranes, cellulose acetate membranes, polyvinyl alcohol membranes and others apparent to one of ordinary skill in the art having a pore size of about 0.1 to 0.5 microns.

The test strip of the present invention may be produced, for example, in the following manner. That is, water-soluble components among the aforementioned components are dissolved in water or others apparent to one of ordinary skill in the art, a carrier is impregnated with the resulting solution, water in the carrier is thoroughly removed by freeze-drying or others methods apparent to one of ordinary skill in the art, and then a fluorescent chromogen that is hardly water-soluble is dissolved in a volatile organic solvent such as methanol, ethanol, ethyl acetate, ether or others apparent to one of ordinary skill in the art, coated on the carrier and quickly dried.

Alternatively, the test strip may be produced by dissolving the aforementioned components in a buffer solution, impregnating a carrier with the resulting solution and then quickly drying the carrier.

The test strip thus prepared may be used by cutting it into small pieces or by adhering it onto a second carrier to provide a cassette-like shape. Also, it is possible to process the test strip on a pad.

When a biological component is determined using the test strip of the present invention, it can be measured, for example, in the following manner.

That is, (1) a predetermined amount of a sample to be tested containing a substance to be measured is spotted on the test strip, (2) after a predetermined period of time, following step (1), and once sufficient soaking of the sample in the test strip has been confirmed, the fluorescence strength is measured by irradiating with a light source of a specified wavelength and by using an appropriate fluorescence measuring apparatus, (3) the difference between the blank value and the fluorescence strength is determined (Δ fluorescence strength), and then (4) the concentration of the substance to be measured in the sample is calculated using a calibration curve prepared by measuring standard amounts of the substance to be measured in a like manner. It is also possible to input in advance a calculation formula into the fluorescence measuring apparatus based on the calibration curve.

Examples of the present invention are given below by way of illustration and not by way of limitation.

Unless otherwise indicated, all parts, ratios, and percents are by weight.

The *Bacillus stearothermophilus* diaphorase I (lot No. 100436) and II (lot No. 100437) used in the present invention were purchased from Seikagaku Kogyo. *Clostridium kluyveri* diaphorase (lot No. D 5540) and porcine heart diaphorase (lot No. D 3752) were purchased from Sigma Chemical. The K values of these diaphorase preparations were 100 or more when measured using dichlorophenolindophenol as a substrate in Tris-HCl buffer (pH 8.0).

Hexokinase/glucose 6-phosphate dehydrogenase (lot No. 737275), glycerokinase (lot No. 691836 or 737267), glycerol 3-phosphate dehydrogenase (lot No. 127779), glycerol dehydrogenase (lot No. 258555), lipase (lot No. 414590) and galactose dehydrogenase (lot No. 104981) were purchased from Boehringer-Mannheim.

Phenylalanine dehydrogenase (lot No. P 4798), alanine dehydrogenase (lot No. A 6425) and fucose dehydrogenase (lot No. H 0400) were purchased from Sigma Chemical.

Leucine dehydrogenase (lot No. 204-36) was purchased from Nacalai Tesque.

Cholesterol dehydrogenase manufactured by Amano Pharmaceutical was used in the following Examples.

The activities of these enzymes were taken from the data attached to the respective products or labels thereof.

Nitrotetrazolium blue (lot No. 298-83-9) was purchased from Dojindo Laboratories. Resazulin (lot No. R 2127) was purchased from Sigma Chemical. Alamar Blue (lot No. 537-33452) was purchased from Wako Pure Chemical Industries. Cellulose powder (lot No. 075-41) was purchased from Nacalai Tesque. Human cholesterol (lot No. 250120) was purchased from Seikagaku Kogyo. The other chemicals used in the following Examples were all reagent grade.

REFERENCE EXAMPLE 1 AND COMPARATIVE EXAMPLE 1

In 50 mM Tris-HCl buffer (pH 8.5) were dissolved 10 U/ml of glycerol dehydrogenase, 5 U/ml of diaphorase and 10 μg/ml of resazulin, each to the final concentration as indicated above. A filter paper (No. 2) manufactured by Whatman was impregnated with 10 μl of the thus prepared solution and then freeze-dried. The freeze-dried filter paper was cut into a small piece having a size of 3×3 mm to obtain a test strip. The test strip thus obtained was fixed at both ends onto a 4×45 mm polystyrene film stick.

A 2 μl portion of aqueous solution containing a predetermined concentration of NADH was spotted on the thus obtained test strip. Two minutes thereafter, the test strip was applied to a fluorescence-measuring apparatus (Shimadzu RF-1500) and the fluorescence strength (580 nm) thereof was measured at an angle of 90° relative to the incident light (Reference Example 1).

Also, for comparison, a test strip was prepared in the same manner as in Reference Example 1, except that the 10 μl/ml of resazulin was replaced by 10 mg/ml of nitrotetrazolium blue.

A 2 μl portion of aqueous solution containing a predetermined concentration of NADH was spotted on the thus obtained test strip and, 2 minutes thereafter, the test strip was applied to a fluorescence-measuring apparatus, and the reflected light strength (475 nm) thereof was measured at an angle of 90° relative to the incident light (Comparative Example 1).

The results are shown in Table 1. Each value in the table indicates the average±standard deviation of six data sets showing the difference between fluorescence strength or reflected light strength and a blank.

TABLE 1

| NADH conc. (μM) | −Δ Reflected light strength (nitrotetrazolium blue) | Δ Fluorescence strength (resazulin) |
|---|---|---|
| 2,500 | 418 ± 31 | |
| 2,000 | 301 ± 26 | |
| 1,500 | 222 ± 10 | |
| 1,000 | 145 ± 13 | |
| 500 | 62 ± 15 | |
| 100 | | 1,450 ± 82 |
| 50 | | 780 ± 50 |
| 25 | | 406 ± 31 |
| 10 | | 150 ± 12 |
| 5 | | 68 ± 9 |
| 0 (blank) | 0 ± 7 | 0 ± 11 |

As shown in Table 1, the use of a test strip containing resazulin as the color coupler provides a sensitivity that is about 100 times higher than that of a test strip containing commonly used nitrotetrazolium blue as the color coupler.

EXAMPLE 1

A test strip for glycerol determination was prepared in the following manner.

That is, a solution containing 2 mM of NADP, 10 mM of magnesium chloride, 15 mM of ammonium sulfate, 15 U/ml of glycerol dehydrogenase, 5 U/ml of diaphorase, 10 μg/ml of resazulin, 1 mg/ml of polyethylene glycol, 10 mg/ml of bovine serum albumin and 0.001 ml/ml of Triton X 100®, each to the final concentration as indicated above, was prepared in 50 mM Tris-HCl buffer (pH 8.7). Using a peristaltic pump, the thus prepared solution was spotted drop by drop (about 20 μl per drop) at intervals of about 1 cm on a polyurethane film of having a width of 5 mm. The resulting film was dried by passing it through a hot air drying zone at a temperature of about 50° C. (passing time, about 2 minutes), and then cut into a 5×5 mm size centering around the spotted part to obtain a test strip. The test strip was then adhered at both ends to a form substrate having a window size of 3×3 mm.

A 2 μl portion of an aqueous solution containing a predetermined concentration of glycerol was spotted on the thus obtained test strip. Five minutes thereafter, the test strip was applied to a fluorescence-measuring apparatus and exposed to a 540 nm light source. The fluorescence strength was measured at 580 nm and at an angle of 90° relative to the incident light. By preparing a calibration curve using the data of Table 1, the amount of glycerol was calculated from the thus obtained fluorescence strength.

Separately, the test strip was stored for 7 days at 40° C. and at a relative humidity of 55%, and then the amount of glycerol was determined in the same manner as described above.

The results are shown in Table 2.

TABLE 2

| Glycerol | Just After Preparation | | After Storage for 7 Days | |
|---|---|---|---|---|
| concentration ($\mu$M) | $\Delta$ Fluorescence strength | Calculated Concentration ($\mu$M) | $\Delta$ Fluorecence strength | Calculated Concentration ($\mu$M) |
| 100 | 1,380 | 93.6 | 1,295 | 87.8 |
| 50 | 752 | 50.6 | 731 | 49.2 |
| 25 | 400 | 26.5 | 351 | 23.3 |
| 10 | 138 | 8.5 | 141 | 8.7 |
| 0 | 0 | 0 | 0 | 0 |

As shown in Table 2, the recovery yield of glycerol is 85 to 106% when using the test strip of the present invention, thus confirming its ability to determine glycerol with high accuracy. Furthermore, the above results show that the test strip of the present invention has excellent storage stability.

EXAMPLE 2

A test strip for phenylalanine determination was prepared in the following manner.

That is, a solution containing 200 mM of potassium chloride, 2.5 mM of NAD, 20 U/ml of phenylalanine dehydrogenase, 5 U/ml of diaphorase, 40 $\mu$l/ml of alamar blue, 0.01 ml/ml of Triton X 100® and 5 mg/ml of gelatin, each to the final concentration as indicated above, was prepared in 200 mM glycine-potassium hydroxide buffer (pH 9.5). Using a Pipette Man, the thus prepared solution was spotted on a polyethylene terephthalate film. After air-drying, a methanol solution containing 1% by volume of vinyl pyrrolidone-vinyl acetate copolymer (20:80 by weight ratio) was coated on the film, and then a small amount of a methanol solution containing 50% by volume cellulose powder was quickly coated thereon. This was dried at 40 to 50° C. to obtain a test strip supported by a polyethylene terephthalate film.

A 5 $\mu$l portion of phenylalanine aqueous solution was spotted on the thus obtained test strip, and fluorescence strength was measured 10 minutes thereafter (excitation wavelength 530 nm, fluorescence wavelength 570 nm).

The results are shown in Table 3. Each value in the table indicates an average±standard deviation of five data points measuring the difference between a blank and fluorescence strength ($\Delta$ fluorescence strength).

TABLE 3

| Phenylalanine Concentration ($\mu$M) | $\Delta$ Fluorescence Strength |
|---|---|
| 100 | 2,103 ± 105 |
| 50 | 1,117 ± 76 |
| 25 | 498 ± 30 |
| 10 | 205 ± 13 |
| 0 (blank) | 0 ± 20 |

From the data shown in Table 3, a highly linear relationship was obtained between the phenylalanine concentration (X) and the $\Delta$ fluorescence strength (Y) as Y=−1.2+21.2X (correlation coefficient, 0.999). Furthermore, the above results show that phenylalanine can be determined with high sensitivity and high accuracy using the test strip of the present invention.

EXAMPLE 3

A test strip for cholesterol determination was prepared in the following manner.

That is, a solution containing 5 mM of NAD, 20 U/ml of cholesterol dehydrogenase, 5 U/ml of diaphorase, 40 $\mu$l/ml of alamar blue and 0.01 ml/ml of Triton X 100®, each to the final concentration as indicated above, was prepared in 200 mM glycine-potassium hydroxide buffer (pH 8.5). Using a Pipette Man, a 2 $\mu$l portion of the thus prepared solution was spotted on a small piece (3×3 mm) of a filter paper (No. 5C) manufactured by Whatman and then freeze-dried to obtain a test strip. The test strip was then adhered to a paper board using a pressure sensitive adhesive double coated tape.

An appropriate amount of human cholesterol was added to a blood plasma sample collected from a healthy male volunteer (aged 35), a 2 $\mu$l portion of the blood plasma sample was spotted on the thus obtained test strip, and then fluorescence strength was measured 10 minutes thereafter (excitation wavelength 530 nm, fluorescence wavelength 570 nm). Also, the concentration of cholesterol in these blood plasma samples was calculated using a separately prepared calibration curve.

The results are shown in Table 4. Each cholesterol concentration in the table indicates an average±standard deviation of five data points.

TABLE 4

| Cholesterol added (mg/dl) | Cholesterol concentration (mg/dl) | Recovery yield (%) |
|---|---|---|
| 300 | 480 ± 25 | 90 |
| 200 | 400 ± 6 | 96 |
| 100 | 310 ± 13 | 101 |
| 50 | 260 ± 16 | 102 |
| 0 (blank) | 209 ± 11 | — |

The results of Table 4 show that cholesterol can be determined with high sensitivity and high accuracy using the test strip of the present invention.

EXAMPLE 4

A test strip for galactose determination was prepared in the following manner.

That is, a solution containing 2.5 mM of NAD, 10 U/ml of galactose dehydrogenase and 10 $\mu$g/ml of resazulin, each to the final concentration as indicated above, was prepared in 100 mM of phosphate-potassium hydroxide buffer (pH 7.5). Using a Pipette Man, a 2 $\mu$l portion of the thus prepared solution was spotted on a small piece (3×3 mm) of a filter paper (No. 2) manufactured by Whatman and then freeze-dried to obtain a test strip. The test strip was then adhered to a paper board using a pressure sensitive adhesive double coated tape.

A 2 $\mu$l portion of galactose aqueous solution was spotted on the thus obtained test strip, and fluorescence strength was measured (excitation wavelength 540 nm, fluorescence wavelength 580 nm).

The results are shown in Table 5. Each value in the table indicates an average±standard deviation of five data points measuring the difference between a blank and fluorescence strength (Δ fluorescence strength).

TABLE 5

| Galactose Conc. ($\mu$M) | Δ Fluorescence Strength |
|---|---|
| 100 | 1,300 ± 95 |
| 50 | 670 ± 76 |
| 25 | 320 ± 26 |
| 10 | 130 ± 18 |
| 0 (blank) | 0 ± 11 |

From the data shown in Table 5, a highly linear relationship was obtained between galactose concentration (X) and the Δ fluorescence strength (Y) as Y=−1.1+13.1X (correlation coefficient, 1.000). Furthermore, the above results show that galactose can be determined with high sensitivity and high accuracy using the test strip of the present invention.

EXAMPLE 5

A test strip for fucose determination was prepared in the following manner.

That is, a solution containing 2.5 mM of NAD, 10 U/ml of fucose dehydrogenase and 10 $\mu$g/ml of resazulin, each to the final concentration as indicated above, was prepared in 100 mM of phosphate-potassium hydroxide buffer (pH 7.5). Using a Pipette Man, a 2 $\mu$l portion of the thus prepared solution was spotted on a small piece (3×3 mm) of a filter paper (No. 2) manufactured by Whatman and then freeze-dried to obtain a test strip. The test strip was then adhered to a paper board using a pressure sensitive adhesive double coated tape.

A 2 $\mu$l portion of fucose aqueous solution was spotted on the thus obtained test strip, and fluorescence strength was measured 10 minutes thereafter (excitation wavelength 540 nm, fluorescence wavelength 580 nm).

The results are shown in Table 6. Each value in the table indicates an average±standard deviation of five data points measuring the difference between a blank and fluorescence strength (Δ fluorescence strength).

TABLE 6

| Fucose Concentration ($\mu$M) | Δ Fluorescence Strength |
|---|---|
| 100 | 1,510 ± 113 |
| 50 | 766 ± 56 |
| 25 | 305 ± 40 |
| 10 | 148 ± 9 |
| 0 (blank) | 0 ± 5 |

From the data shown in Table 6, a highly linear relationship was obtained between the fucose concentration (X) and the Δ fluorescence strength (Y) as Y=−19.2+15.3X (correlation coefficient, 0.997). Furthermore, the above results show that fucose can be determined with high sensitivity and high accuracy using the test strip of the present invention.

EXAMPLE 6

A test strip for alanine determination was prepared in the following manner.

That is, a solution containing 2.5 mM of NAD, 10 U/ml of alanine dehydrogenase and 10 $\mu$g/ml of resazulin, each to the final concentration as indicated above, was prepared in 100 mM of phosphate-potassium hydroxide buffer (pH 7.5). Using a Pipette Man, a 2 $\mu$l portion of the thus prepared solution was spotted on a small piece (3×3 mm) of a filter paper (No. 2) manufactured by Whatman and then freeze-dried to obtain a test strip. The test strip was then adhered to a paper board using a pressure sensitive adhesive double coated tape.

A 2 $\mu$l portion of alanine aqueous solution was spotted on the thus obtained test strip, and fluorescence strength was measured (excitation wavelength 540 nm, fluorescence wavelength 580 nm).

The results are shown in Table 7. Each value in the table indicates an average±standard deviation of five data points measuring the difference between a blank and fluorescence strength (Δ fluorescence strength).

TABLE 7

| Alanine Concentration ($\mu$M) | Δ Fluorescence Strength |
|---|---|
| 100 | 1,430 ± 70 |
| 50 | 781 ± 75 |
| 25 | 374 ± 28 |
| 10 | 147 ± 21 |
| 0 (blank) | 0 ± 11 |

From the data shown in Table 7, a highly linear relationship was obtained between alanine concentration (X) and the Δ fluorescence strength (Y) as Y=14.1+14.4X (correlation coefficient, 0.998). Furthermore, the above results show that alanine can be determined with high sensitivity and high accuracy using the test strip of the present invention.

EXAMPLE 7

A test strip for leucine determination was prepared in the following manner.

That is, a solution containing 2.5 mM of NAD, 10 U/ml of leucine dehydrogenase and 10 $\mu$g/ml of resazulin, each to the final concentration indicated above, was prepared in 50 mM of phosphate-potassium hydroxide buffer (pH 7.5). Using a Pipette Man, a 2 $\mu$l portion of the thus prepared solution was spotted on a small piece (3×3 mm) of a filter paper (No. 2) manufactured by Whatman and then freeze-dried to obtain a test strip. The test strip was then adhered to a paper board using a pressure sensitive adhesive double coated tape.

A 2 $\mu$l portion of leucine aqueous solution was spotted on the thus obtained test strip, and fluorescence strength was measured 10 minutes thereafter (excitation wavelength 540 nm, fluorescence wavelength 580 nm).

The results are shown in Table 8. Each value in the table indicates an average±standard deviation of five data points measuring the difference between a blank and fluorescence strength (Δ fluorescence strength).

TABLE 8

| Leucine Concentration ($\mu$M) | Δ Fluorescence Strength |
|---|---|
| 100 | 1,803 ± 110 |
| 50 | 923 ± 77 |
| 25 | 499 ± 25 |
| 10 | 221 ± 8 |
| 0 (blank) | 0 ± 1 |

From the data shown in Table 8, a highly linear relationship was obtained between the leucine concentration (X) and the Δ fluorescence strength (Y) as Y=30.2+17.8X (correlation coefficient, 0.999). Furthermore, the above results show that leucine can be determined with high sensitivity and high accuracy using the test strip of the present invention.

EXAMPLE 8

A test strip for glucose determination was prepared in the following manner.

That is, a solution containing 2.5 mM of NADP, 2.5 mM of ATP, 10 U/ml of hexokinase and glucose 6-phosphate dehydrogenase and 10 µg/ml of resazulin, each to the final concentration indicated above, was prepared in 100 mM of phosphate-potassium hydroxide buffer (pH 7.5). Using a Pipette Man, a 2 µl portion of the thus prepared solution was spotted on a small piece (3×3 mm) of a filter paper (No. 2) manufactured by Whatman and then freeze-dried to obtain a test strip. The test strip was then adhered to a paper board using a pressure sensitive adhesive double coated tape.

A 2 µl portion of glucose aqueous solution was spotted on the thus obtained test strip, and fluorescence strength was measured 10 minutes thereafter (excitation wavelength 540 nm, fluorescence wavelength 580 nm).

The results are shown in Table 9. Each value in the table indicates an average±standard deviation of five data points measuring the difference between a blank and fluorescence strength (Δ fluorescence strength).

TABLE 9

| Glucose Concentration (µM) | Δ Fluorescence Strength |
| --- | --- |
| 100 | 1,105 ± 85 |
| 50 | 612 ± 55 |
| 25 | 278 ± 22 |
| 10 | 109 ± 18 |
| 0 (blank) | 0 ± 11 |

From the data shown in Table 9, a highly linear relationship was obtained between the glucose concentration (X) and the Δ fluorescence strength (Y) as Y=30.2+17.8X (correlation coefficient, 0.999). Furthermore, the above results show that glucose can be determined with high sensitivity and high accuracy using the test strip of the present invention.

While the invention has been described in detail and with reference to specific examples thereof, it will be apparent to one skilled in the art that various changes and modifications can be made therein without departing from the spirit and scope thereof.

What is claimed is:

1. A test strip which comprises a carrier, a dehydrogenase, diaphorase, a fluorescent chromogen, and NAD or NADP.

2. The test strip of claim 1 for measuring a substance, wherein the substance to be measured is a substrate of the dehydrogenase.

3. The test strip of claim 1 for measuring a substance, further comprising one or more enzymes which convert the substance to be measured into a substance which is a substrate of the dehydrogenase.

4. The test strip of claim 1 for measuring a substance selected from the group consisting of glucose 6-phosphate, glycerophosphoric acid, glycerol, phenylalanine, leucine, alanine, androsterone, cholesterol and fucose, and the dehydrogenase is specific for catalyzing the removal and transfer of hydrogen from the substance to be measured or from a product derived from the substance to be measured.

5. The test strip of claim 1, wherein the fluorescent chromogen is selected from the group consisting of resazulin and alamar blue.

6. The test strip of claim 1, impregnated with (i) a diaphorase solution having an activity of from 0.1 to 1,000,000 units per liter in an amount of from 1 to 1,000 µl per 100 cm$^2$ of the test strip; and (ii) a dehydrogenase solution having an activity of from 0.1 to 1,000,000 units per liter in an amount of from 1 to 1,000 µl per 100 cm$^2$ of the test strip.

7. The test strip of claim 1, impregnated with a NAD or NADP solution having a concentration of from 0.001 to 200 mM in an amount of from 0.1 to 10,000 µl per 100 cm$^2$ of the test strip.

8. The test strip of claim 1, wherein in the carrier is selected from the group consisting of paper, non-woven fabric and a membrane filter.

9. The test strip of claim 1 for measuring glycerol, wherein the dehydrogenase comprises glycerol dehydrogenase and the fluorescent chromogen comprises resazulin.

10. The test strip of claim 1 for measuring phenylalanine, wherein the dehydrogenase comprises phenylalanine dehydrogenase and the fluorescent chromogen comprises alamar blue.

11. The test strip of claim 1 for measuring cholesterol, wherein the dehydrogenase comprises cholesterol dehydrogenase and the fluorescent chromogen comprises alamar blue.

12. The test strip of claim 1 for measuring galactose, wherein the dehydrogenase comprises galactose dehydrogenase and the fluorescent chromogen comprises resazulin.

13. The test strip of claim 1 for measuring fucose, wherein the dehydrogenase comprises fucose dehydrogenase and the fluorescent chromogen comprises resazulin.

14. The test strip of claim 1 for measuring alanine, wherein the dehydrogenase comprises alanine dehydrogenase and the fluorescent chromogen comprises resazulin.

15. The test strip of claim 1 for measuring leucine, wherein the dehydrogenase comprises leucine dehydrogenase and the fluorescent chromogen comprises resazulin.

16. The test strip of claim 1 for measuring glucose, further comprising ATP and hexokinase wherein, the dehydrogenase comprises glucose 6-phosphate dehydrogenase and the fluorescent chromogen comprises resazulin.

17. The test strip of claim 1, further comprising one or more of a buffer, an activating agent, a stabilizing agent and a viscosity-improving agent.

18. A test kit comprising a test strip disposed on a substrate, wherein the test strip comprises a carrier, a dehydrogenase, diaphorase, a fluorescent chromogen, and NAD or NADP.

19. The test kit of claim 18, wherein the substrate is selected from the group consisting of polystyrene film, polyethylene terephthalate film and paper board.

20. A method for measuring the concentration of a substance in a sample, said method comprising the steps of:

(1) spotting a predetermined amount of a sample containing a substance on the test strip, said test strip comprising a carrier, a dehydrogenase, diaphorase, a fluorescent chromogen, and NAD or NADP, (2) after sufficient soaking of the sample in the test strip, the fluorescence strength of the reduced fluorescent chromogen is measured by irradiating the test strip with a light source of a specified wavelength, (3) the difference between the blank value and the fluorescence strength is determined, and (4) the concentration of the substance in the sample is calculated using a calibration curve.

* * * * *